United States Patent
Qi et al.

(10) Patent No.: US 11,746,071 B1
(45) Date of Patent: Sep. 5, 2023

(54) OLEFIN METATHESIS IN A LOOP REACTOR

(71) Applicant: Chevron Phillips Chemical Company LP, The Woodlands, TX (US)

(72) Inventors: Wei Qi, Kingwood, TX (US); Enrique Mancillas, Houston, TX (US); Jeffery C. Gee, Kingwood, TX (US); Sean K. McLaughlin, Houston, TX (US); Jared Fern, Kingwood, TX (US); Steven Bischof, Spring, TX (US); Paul Hobson, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/937,558

(22) Filed: Oct. 3, 2022

(51) Int. Cl.
*C07C 6/04* (2006.01)
*B01J 19/18* (2006.01)

(52) U.S. Cl.
CPC ............. *C07C 6/04* (2013.01); *B01J 19/1837* (2013.01)

(58) Field of Classification Search
CPC ................................ C07C 6/04; B01J 19/1837
See application file for complete search history.

(56) References Cited

U.S. PATENT DOCUMENTS

| | | |
|---|---|---|
| 3,652,703 A | 3/1972 | Regier |
| 4,071,471 A | 1/1978 | Banks |
| 5,952,533 A * | 9/1999 | Fischer ................. C07C 29/132 |
| | | 568/865 |
| 7,994,376 B2 | 8/2011 | Small |
| 8,791,312 B2 | 7/2014 | Randolph |
| 10,407,360 B2 | 9/2019 | Small |
| 10,513,473 B2 | 12/2019 | Kreischer |
| 10,519,077 B2 | 12/2019 | Kreischer |
| 10,544,070 B2 | 1/2020 | Small |
| 10,604,457 B2 | 3/2020 | Bischof |
| 10,927,054 B2 | 2/2021 | Kreischer |
| 2008/0103346 A1 | 5/2008 | Burdett |

\* cited by examiner

*Primary Examiner* — Thuan D Dang
(74) *Attorney, Agent, or Firm* — Klemchuk PLLC (57) ABSTRACT

Metathesis of olefins in a loop reactor having liquid reaction medium circulated therein that contains reactant olefins and homogeneous metathesis catalyst system in liquid phase. Recovery of product olefin(s) occurs after removing a liquid reactor effluent from the loop reactor, and unreacted reactant olefin(s) recovered from the liquid reactor effluent can be recycled to the loop reactor.

20 Claims, 3 Drawing Sheets

OLEFIN METATHESIS IN A LOOP REACTOR

FIELD OF THE DISCLOSURE

The present disclosure generally relates to metathesis reactions, and more particularly to the metathesis of olefins in a loop reactor.

BACKGROUND

Olefinic products can be produced by metathesis. Metathesis generally involves contacting one or more reactant olefins in the presence of a metathesis catalyst to form at least one olefinic product that is different from the one or more reactant olefins. Self-metathesis involves contacting one molecule of reactant olefin with a second molecule of the same reactant olefin to form one or more olefinic products that are different from the reactant olefin. Cross-metathesis involves contacting a molecule of a first reactant olefin with a molecule of a second reactant olefin to form one or more olefinic products different from the reactant olefins.

Metathesis of linear olefins in a continuous stirred tank reactor (CSTR) can include a liquid phase that is mixed with an impeller. An inert gas blanket (e.g., nitrogen blanket) can be added to the CSTR, to keep water vapor and oxygen that would otherwise occupy the vapor space above the liquid surface from mixing into the liquid phase. Impeller design and the inert gas blanket present challenges for large scale metathesis production.

There is a need for a metathesis process than can be performed on a large scale and in which the shortcomings of CSTR reactors are addressed.

SUMMARY

A process for olefin metathesis in a loop reactor can include reacting, in the loop reactor, a first reactant olefin in a presence of a homogeneous metathesis catalyst system to form a metathesis product comprising a first product olefin (a light product olefin) and, in some aspects, a second product olefin (a heavy product olefin). Metathesis that is accomplished by the process can be performed on a continuous, as opposed to batch, basis. A liquid reactor effluent containing the first product olefin (e.g., the light product olefin) and, in some aspects, the second product olefin (e.g., the heavy product olefin), can be removed from the loop reactor on a continuous basis for subsequent separation of the product olefin(s) in a first product separation zone, a catalyst separation zone, and, in some aspects, a second product separation zone. In some aspects, the process can include a second reactant olefin that reacts in the loop reactor in the presence of the homogeneous metathesis catalyst system to form the metathesis product.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Illustrative aspects of the subject matter claimed herein will now be disclosed. In the interest of clarity, not all features of an actual implementation are described in this specification. It can be appreciated that in the development of any such actual aspect, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

The term "contact" and its derivatives as used herein refers to any addition sequence, order, or concentration for contacting or combining two or more components of the disclosed embodiments.

The term "stream" as used herein refers to a composition of the components disclosed herein for the respective stream. The term "stream" can additionally refer to and imply associated equipment, such as conduit, line, and pipe that is used to move the composition from one location to another (e.g., a stream from one equipment unit to another equipment unit).

The term "olefin" as used herein refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" as used herein refers to a linear aliphatic mono-olefin having a carbon-carbon double bond between the first and second carbon atoms. It is noted that "normal alpha olefin" is not synonymous with "linear alpha olefin" as the term "linear alpha olefin" can additionally include linear olefinic compounds having a double bond between the first and second carbon atoms and additional double bonds.

Terms that refer to a state of matter, such as solid, liquid, liquid portion, gas, vapor, vapor portion, solid phase, liquid phase, gas phase, and vapor phase, refer to the state of matters under the operating conditions in the respective step of the disclosed processes. For example, "liquid phase" or "liquid" in context of i) the loop reactor disclosed herein refers to a liquid being present at the temperature and pressure at which the metathesis reaction occurs in the loop reactor, and ii) streams, lines, conduits that exist between any equipment of the apparatuses disclosed herein refers to a liquid being present at the temperature and pressure in said streams, lines, and conduits. Similarly, "vapor phase" or "vapor" in context of i) a product separation zone disclosed herein refers to a gas or vapor being present at the temperature and pressure at which the product separation occurs in a product separation zone, and ii) streams, lines, conduits that exist between any equipment of the apparatuses disclosed herein refers to a vapor or gas being present at the temperature and pressure in said streams, lines, and conduits.

Disclosed herein are processes and apparatuses for metathesis of olefins utilizing a homogeneous metathesis catalyst system in a loop reactor. The metathesis reaction occurs in a liquid phase, e.g., in the liquid reaction medium disclosed herein. The liquid reaction medium is circulated in the loop reactor, and reaction occurs while the liquid reaction medium is circulated. Utilizing the metathesis reaction in liquid phase, and only having liquid phase present in the loop reactor (the reactor being liquid-full), allows for a continuous metathesis process and apparatus that can operate on a large scale. Using a homogeneous catalyst instead of a heterogeneous catalyst allows the metathesis catalyst to be mixed into the same phase, e.g., the liquid phase, as the reactant olefins. Further, using two separation zones improves separation performance because the reactor effluent can be divided into a first part that is generally includes lighter reactant olefin and product olefin components and a heavier part that includes heavier reactant olefin and product olefin as well as the homogeneous metathesis catalyst system. Further still, mixing can be accomplished in the loop reactor without moving parts in the pipe segments of the loop reactor. Moreover, the disclosed processes and apparatus are not limited by the number of reactant olefins or the number of product olefins, nor by the relative carbon numbers of the reactant olefins compared to the product olefins. The disclosed process and apparatus are particularly suitable for forming a metathesis product that contains a product olefin having a boiling point that is close to a boiling point of one or more of the reactant olefins, because close-boiling reactant and product olefins can be separated in one or more product separation zones that are downstream of the loop reactor.

Figure 1:
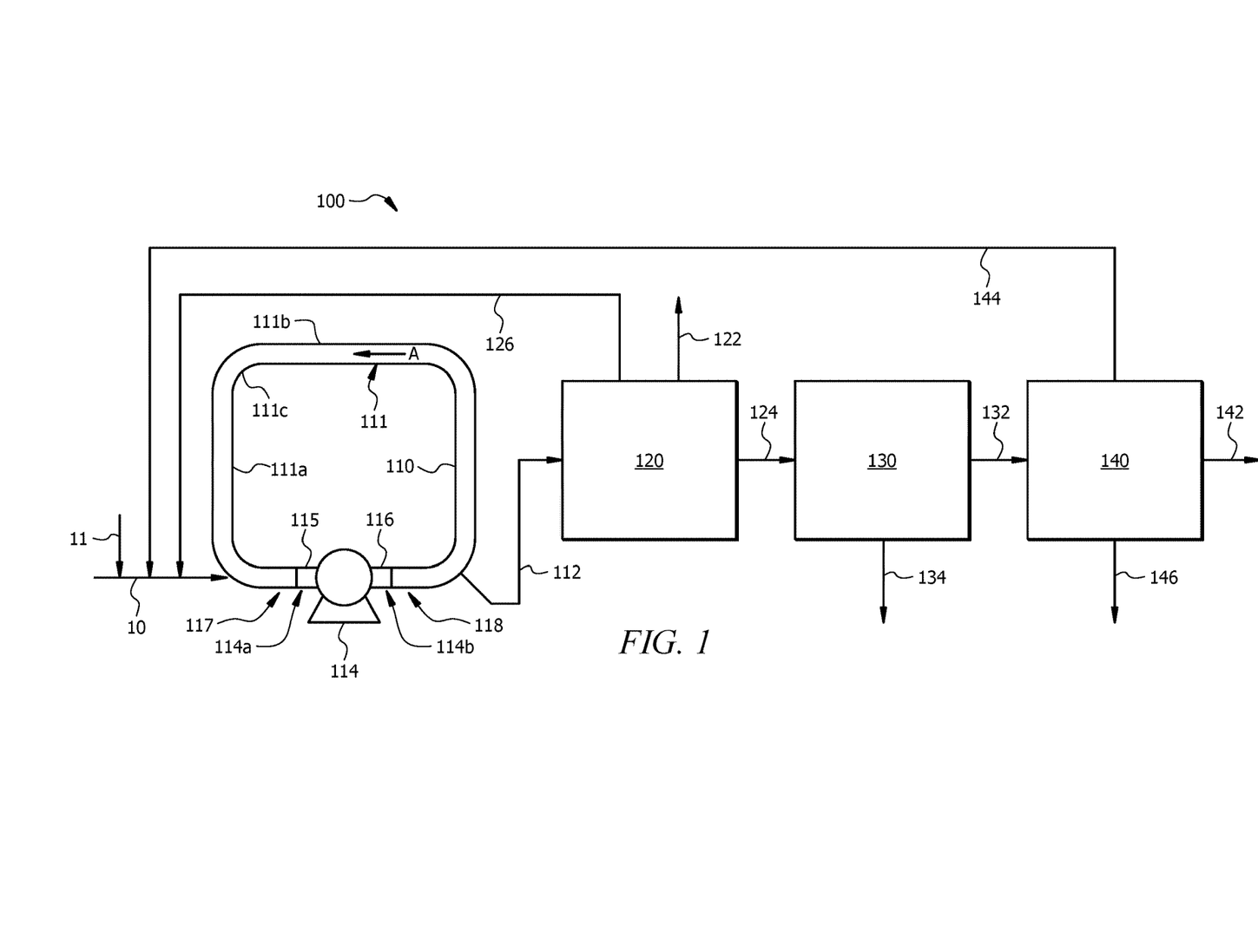
FIG. 1 illustrates a schematic diagram of a metathesis reaction process disclosed herein.

FIG. 1 illustrates a schematic diagram of a metathesis reaction process 100 disclosed herein. Steps of the process 100 take place in a loop reactor 110, a first product separation zone 120, a catalyst separation zone 130, and a second product separation zone 140. A reactor effluent stream 112 is fluidly connected to the loop reactor 110 and to the first product separation zone 120, the first product separation zone 120 is fluidly connected to the loop reactor 110 via at least one other stream (e.g., recycle stream 126) and to the catalyst separation zone 130 via stream 124. The catalyst separation zone 130 is fluidly connected to the second product separation zone 140 via stream 132. The second product separation zone 140 is fluidly connected to the loop reactor 110 via at least one stream (e.g., recycle stream 144). In embodiments, the first product separation zone 120 can include two separators (e.g., separators 220 and 225 in FIGS. 2 and 3). In some aspects, the two separators of the first product separation zone 120 can include a compressor 221 between the separators 220 and 225 (e.g., see FIG. 3).

Figure 2:
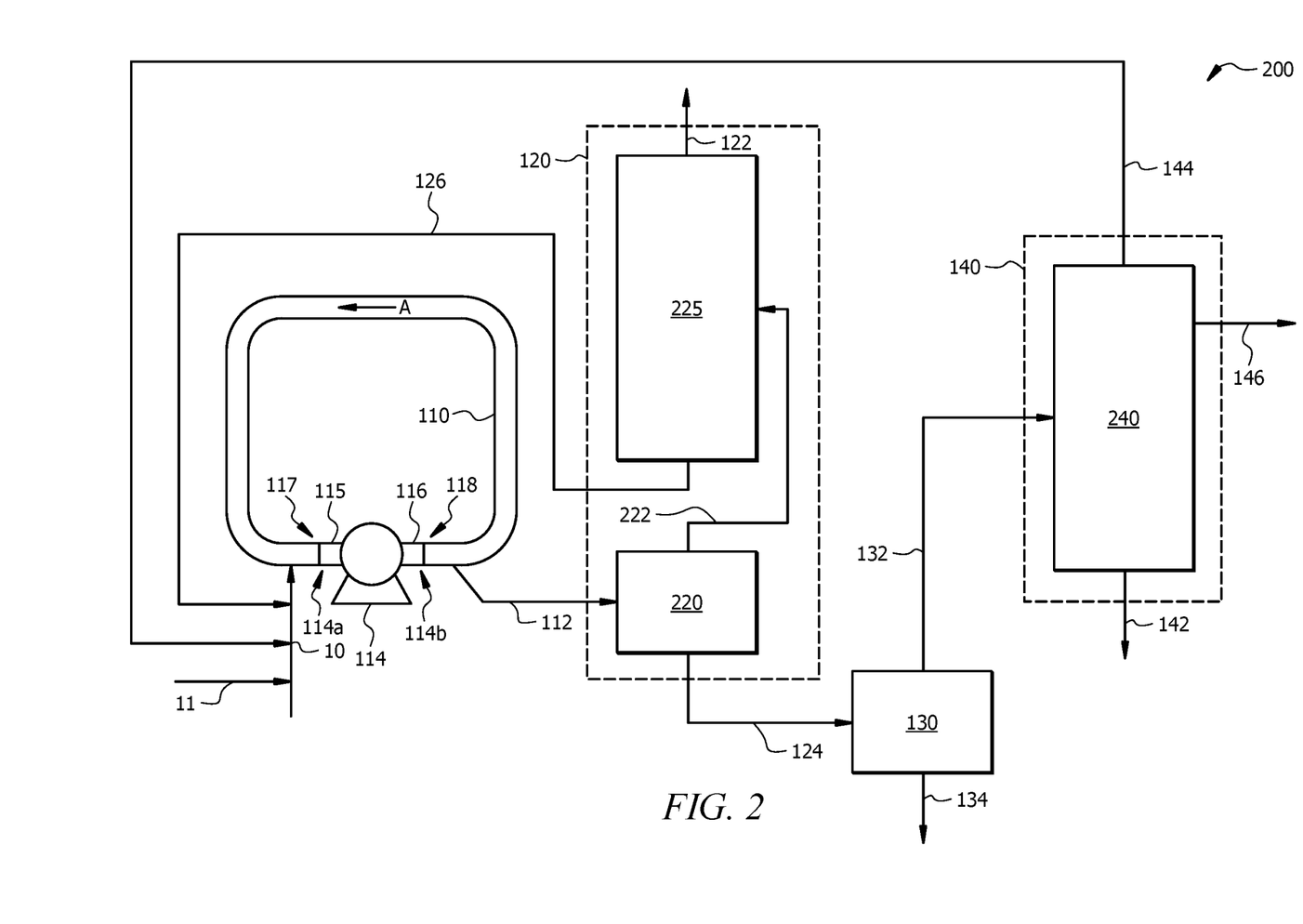
FIG. 2 illustrates a schematic diagram of an apparatus for performing the olefin metathesis process of FIG. 1.
Figure 3:
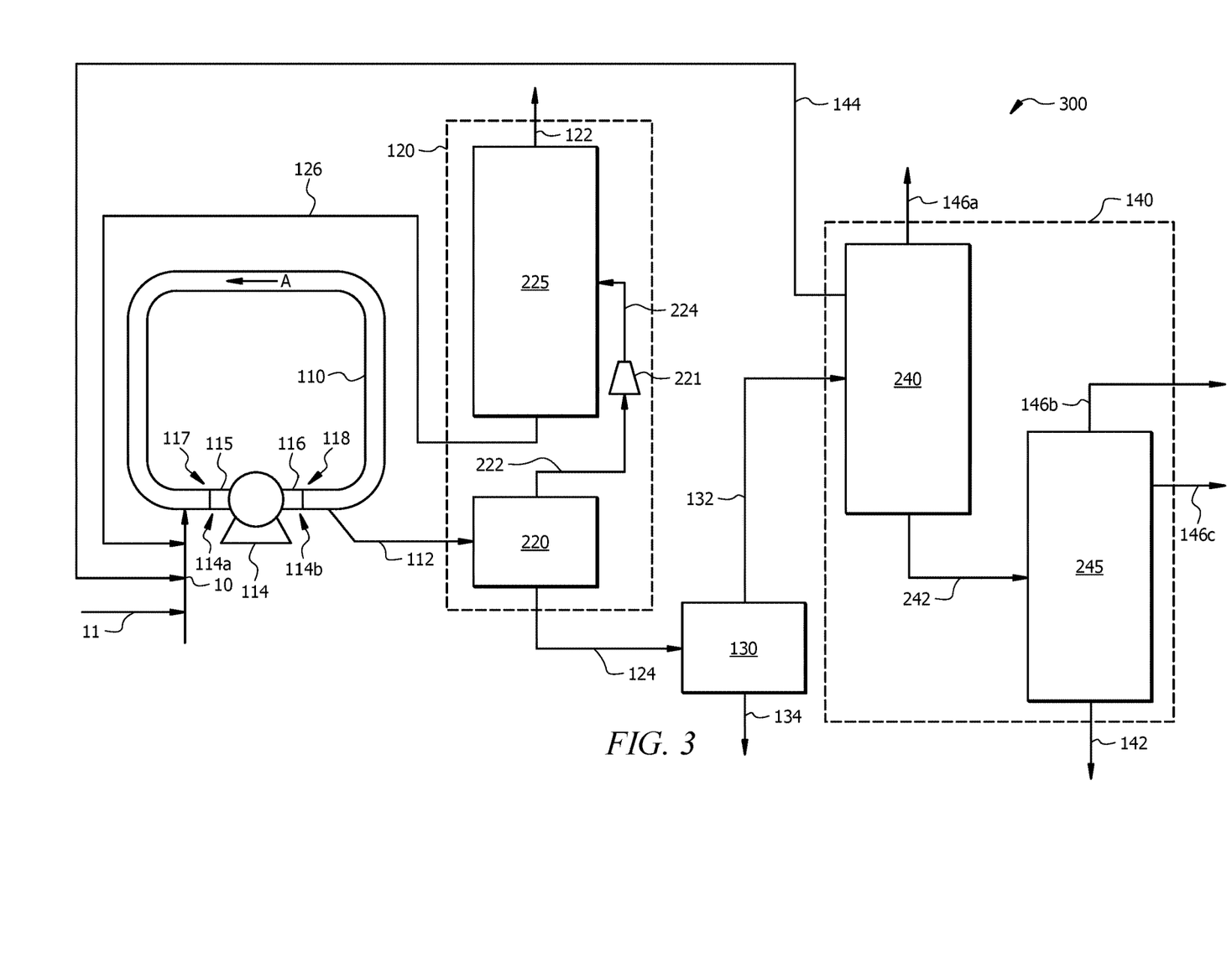
FIG. 3 illustrates a schematic diagram of another apparatus for performing the olefin metathesis process of FIG. 1.

In embodiments, the second product separation zone 140 can include one separator (e.g., separator 240 in FIG. 2) or two separators (e.g., separators 240 and 245 in FIG. 3).

The process 100 generally begins with introducing reaction components to the loop reactor 110. The reaction components can include one reactant olefin (a reactant olefin), two reactant olefins (a first reactant olefin and a second reactant olefin), or more than two reactant olefins (e.g., a mixture of olefins). Use of "reactant olefin(s)" herein is intended to include both of these aspects and embodiments. Thus, in some aspects the process 100 can include introducing a first reactant olefin to the loop reactor 110; and other aspects can include introducing a first reactant olefin and a second reactant olefin to the loop reactor 110; and yet other aspects can include introducing multiple reactant olefins to the loop reactor 110. Introducing the reaction components can be performed in the process 100 on a continuous basis.

Reactant olefin(s) can be introduced to the loop reactor 110 via feed stream 10. In some aspects, the reactant olefin includes one olefin; alternatively, the reactant olefins include two olefins; alternatively, the reactant olefin(s) can include three or more olefins. When two different reactant olefins are employed, the molar ratio of a first reactant olefin to a second reactant olefin can be in a range of from about 0.8:1 to about 1.2:1; alternatively, the molar ratio of a first reactant olefin to a second reactant olefin can be about 1:1. When two different reactant olefins are employed, the first reactant olefin and the second reactant olefin can be introduced to the loop reactor 110 via feed stream 10; alternatively, the first reactant olefin can be introduced to the loop reactor 110 via feed stream 10 and the second reactant olefin can be introduced to the loop reactor 110 via a separate stream that is fluidly connected to the loop reactor 110.

One or more of the reactant olefin(s) in the feed stream 10 can be selected from any olefin having 2, 3, 4, 5, 6, 7, 8, 9, 10, 11, 12, 13, 14, 15, 16, 17, 18, 19, or 20 carbon atoms; additionally or alternatively, one or more reactant olefin(s) in the feed stream 10 can be selected from any olefin that is an alpha olefin; additionally or alternatively, one or more reactant olefin(s) in the feed stream 10 can be selected from an olefin that is a normal alpha olefin. Specific nonlimiting examples of reactant olefin(s) can include, but are not limited to, 1-butene, 1-pentene, 1-hexene, 1-heptene, 1-octene, 1-nonene, 1-decene, 1-undene, 1-dodecene, 1-tridecene, 1-tetradecene, 1-butene in combination with a higher carbon number olefin, or 1-hexene in combination with a higher carbon number olefin, or combinations thereof.

In additional aspects, the process 100 can include introducing the homogeneous metathesis catalyst system to the loop reactor 110. In some aspects, the homogeneous metathesis catalyst system can be introduced via stream 10, while in other aspects the homogeneous metathesis catalyst system is introduced in a stream that is separate and different than stream 10. For example, the homogeneous metathesis catalyst system can be contained in a catalyst stream 11 that combines with the feed stream 10 that introduces the reactant olefin(s) and the homogeneous metathesis catalyst system to the loop reactor 110. Alternatively, catalyst stream 11 can be configured to feed the homogeneous metathesis catalyst system to the loop reactor 110 separately from the reactant olefin(s) in the feed stream 10.

Any suitable homogeneous metathesis catalyst system can be used. The homogeneous metathesis catalyst system generally includes a metathesis catalyst dissolved in an inert solvent, such as toluene. Non-limiting examples of the homogeneous metathesis catalyst system can include a metal oxide based metathesis catalyst system, a metal halide based metathesis catalyst system, a metal carbene based metathesis catalyst system (also referred to as a Grubbs catalyst based catalyst system), or any combination thereof. In one aspect, the metathesis catalyst system can be a metal oxide based metathesis catalyst system or a metal halide based metathesis catalyst system; alternatively, a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina (MoO3/Al2O3), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), or rhenium oxide on alumina activated with tetramethyl tin ($Re_2O_7/Al_2O_3/SnMe_4$). Other suitable metal oxide based metathesis catalyst systems are known to those skilled in the art.

The metal oxide based metathesis catalyst system can further include a metal alkyl activator. In an aspect, the metal alkyl can comprise, can consist essentially of, or can be an alkyl lithium, an alkyl magnesium, an alkyl aluminum, alkyl tin compounds, or any mixture thereof. In an aspect, the metal alkyl activator can be an alkyl lithium compound. In another aspect, the metal alkyl activator can comprise, can consist essentially of, or can be an alkyl magnesium compound; alternately an alkyl aluminum compound; or alternatively, an alkyl tin compound. Non-limiting examples of alkyl aluminum compounds can include trialkyl aluminum compounds and/or alkyl aluminum halide compounds. The alkyl groups on the metal alkyl activator can include any C1 to C10 hydrocarbyl group, or alternatively, any C1 to C5 hydrocarbyl group. In various embodiments, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, triisobutylaluminum, or combinations thereof. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, ethylaluminum sesquichloride, or combinations thereof. Suitable and non-limiting examples of alkyl tin compounds can include tetramethyl tin, tetraethyl tin, tetrabutyl tin, or combinations thereof.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten; or alternatively, a halide of molybdenum. The halide of the metal halide based metathesis catalyst system can be chloride, bromide, or iodide. In an aspect, the halide can comprise, consist essentially of, or can be, chloride; alternatively, bromide; or alternatively, iodide. Hence, the metal halide based metathesis catalyst system can comprise (or consist essentially of, or consist of) tungsten chloride, molybdenum chloride, or a mixture thereof; alternatively, tungsten chloride; or alternatively, molybdenum chloride.

Optionally, the metal halide based metathesis catalyst system can further comprise a metal alkyl activator (as described herein), oxygen, an alcohol, or any combination thereof; alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethylaluminum dichloride/ethyl alcohol ($WCl_6/EtAlCl_2/EtOH$), molybdenum chloride/triethyl aluminum ($MoCl_5/AlEt_3$), or molybdenum chloride/triethyl aluminum/$O_2$ ($MoCl_5/AlEt_3/O_2$). Other suitable metal halide based metathesis catalyst systems are known to those skilled in the art.

The metal of the metal carbene based metathesis catalyst systems can comprise (or consist essentially of, or consist of) tungsten, tantalum, osmium, molybdenum, ruthenium, or any combination thereof. For instance, the metal of the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

In aspects, the process 100 can include circulating, in the loop reactor 110, a liquid reaction medium comprising a first reactant olefin and a homogeneous metathesis catalyst system; alternatively, the process 100 can include circulating, in the loop reactor 110, a liquid reaction medium comprising a first reactant olefin, a second reactant olefin, and a homogeneous metathesis catalyst system. Once reaction begins, the circulated liquid reaction medium can include a first product olefin; alternatively, the circulated liquid reaction medium can include a first product olefin and a second product olefin; alternatively, the circulated liquid reaction medium can include a first product olefin, a second product olefin, and a third product olefin. In other aspects, the circulated liquid reaction medium can include three or more reactant olefins and two or more product olefins. In additional aspects, the first product olefin, second product olefin, and optional third product olefin can be in a mixture having a distribution of multiple product olefins, where the first product olefin and second product olefin are the target product olefins.

In aspects, the loop reactor 110 is operated as liquid full. "Liquid full" as used herein for the loop reactor 110 refers to the loop reactor 110 being full of liquid, e.g., in the form of the liquid reaction medium. That is, aspects and embodiments contemplate that no vapor is generated in the metathesis reaction, and all metathesis reaction occurs in liquid phase. Unlike other reactor configurations, loop reactor 110 does not have a vapor space for produced vapor product olefins, and in this sense, the loop reactor 110 can be "liquid full."

The loop reactor 110 can be formed of one or more pipe segments 111 such that a flowpath A is formed in the loop reactor 110. The loop reactor 110 can also include a circulation pump 114 that has an inlet 115 connected to an outlet 117 of the flowpath A and an outlet 116 connected to an inlet 118 of the flowpath A.

The one or more pipe segments 111 can include linear vertical pipe segments 111a, one or more horizontal pipe segments 111b, and curved pipe segments (e.g., elbows 111c). In some aspects, each linear vertical pipe segment 111a can be coupled to another linear vertical pipe segment 111a by a horizontal pipe segment 111b and elbows 111c; alternatively, the linear vertical pipe segments 111a can be coupled with one another via a U-shaped horizontal pipe segment (not shown) rather than a linear horizontal pipe segment 111b and elbows 111c. In some aspects, the linear vertical pipe segments 111a or the horizontal pipe segments 111b can include heat exchange jackets wrapped around at least a portion of the segments 111a or segments 111b, that can be used to control the temperature of the liquid reaction medium in the loop reactor 110.

The circulation pump 114 is configured to receive the liquid reaction medium via the inlet 115, and to provide a motive force against the liquid reaction medium as the liquid reaction medium leaves the outlet 116 of the pump 114, circulating the liquid reaction medium in the loop reactor 110 through the flowpath A and back to the inlet 115 of the pump 114. The circulation pump 114 can be embodied as any type of liquid pump having components that are inert relative to the components in the liquid reaction medium and capable of providing motive force under the metathesis reaction conditions disclosed herein.

The feed stream 10 can be coupled to the loop reactor 110 via one of the one or more pipe segments 111 on the suction side 114a of the pump 114 such that reaction components mix into the circulating liquid reaction medium before entering the inlet 115 of the pump 114; alternatively, the feed stream 10 can be coupled to the inlet 115 of the pump 114. In aspects where the catalyst system or recycled olefin is fed to the loop reactor 110 at a location different than where the feed stream 10 is connected to the loop reactor 110, such location can connect to the loop reactor 110 via one of the one or more pipe segments 111 on the suction side 114a of the pump 114 such that the catalyst system or recycled olefin mixes into the circulating liquid reaction medium before entering the inlet 115 of the pump 114; alternatively, the stream containing the catalyst system or recycled olefin can be coupled to the inlet 115 of the pump 114.

In aspects, the circulation pump 114 and the velocity of circulation of the liquid reaction medium in the flowpath A in the loop reactor 110 can be sufficient to mix the components in the liquid reaction medium. The mixing can facilitate dissolution of light reactant olefin and/or light product olefin (e.g., ethylene or propylene) into the liquid reaction medium. While an impeller may be used inside the circulation pump 114 to provide motive force to the liquid reaction medium for circulation, mixing of the liquid reaction medium in flowpath A of the loop reactor 110 does not utilize moving parts (e.g., does not have an impeller in the flowpath A) and does not rely on the size of the impeller compared to the mixing that occurs in a CSTR. While motive force provided by the circulation pump 114 can contribute to mixing, mixing in the loop reactor 110 is also accomplished by circulation of the liquid reaction medium in the flowpath A. As such, challenges relating to the impeller for utilizing a CSTR on a large scale application are addressed by using the loop reactor 110 disclosed herein.

The reactant olefin(s) and homogeneous metathesis catalyst system can be introduced to the loop reactor 110 via one or more reactor inlets by any technique known in the art with the aid of this disclosure, e.g., a control valve in feed stream 10.

The process 100 can include reacting, in the loop reactor 110, the first reactant olefin in a presence of the homogeneous metathesis catalyst system to form the metathesis product containing a first product olefin and a second product olefin; alternatively, reacting, in the loop reactor 110, the first reactant olefin and the second reactant olefin in a presence of the homogeneous metathesis catalyst system to form the metathesis product containing the first product olefin; alternatively, reacting, in the loop reactor 110, the first reactant olefin and the second reactant olefin in a presence of the homogeneous metathesis catalyst system to form the metathesis product containing the first product olefin and the second product olefin; alternatively, reacting, in the loop reactor 110, the first reactant olefin and the second reactant olefin in a presence of the homogeneous metathesis catalyst system to form the metathesis product containing the first product olefin, the second product olefin, and the third product olefin; alternatively, reacting, in the loop reactor 110, one, two, or more than two reactant olefins in a presence of the homogeneous metathesis catalyst system to form the metathesis product containing the multiple product olefins containing at least one target product olefin.

In aspects, the liquid reaction medium in the loop reactor 110 does not include a heterogeneous metathesis catalyst or a heterogeneous metathesis catalyst system. That is, embodiments contemplate that the metathesis catalyst remains dissolved in liquid while in the loop reactor 110.

Contacting the reactant olefin(s) in the presence of the homogeneous metathesis catalyst system in the loop reactor 110 (in liquid phase) converts at least a portion of the total amount of reactant olefin(s) in the loop reactor 110 to metathesis product. The metathesis product can contain a first product olefin (e.g., ethylene or propylene); alternatively, the metathesis product can contain a first product olefin (e.g., the light metathesis product, for example, ethylene or propylene) and a second olefin (e.g., the heavy metathesis product). The metathesis product, in some embodiments, can also include a third product olefin (e.g., another heavy metathesis product). Other olefin products can also be produced in amounts smaller than the amounts produced for the product olefin(s) described herein, creating a distribution of product olefins which can be subject to separation to isolate target product olefin(s).

The loop reactor 110 can be operated at any conditions capable of forming a metathesis product in a liquid reaction medium as disclosed herein. Metathesis conditions capable of forming a metathesis product can include, but are not limited to, pressure, temperature, time, and concentration (in relations to solution phase formation of the metathesis product) and are independently described herein. These independently described conditions can be utilized in any combination and without limitation, to further describe the process disclosed herein.

In aspects, the process 100 can utilize any pressure capable of forming a metathesis product in a liquid reaction medium as disclosed herein, where the metathesis product is in liquid phase. In an aspect, a minimum pressure which can be utilized to form the metathesis product (or the liquid metathesis product) can be 5 psia (34.5 kPa), 10 psia (68.9 kPa), 14 psia (96.5 kPa), 14.7 psia (101.4 kPa), 20 psia (138.9 kPa), or 50 psia (344.7 kPa); alternatively or additionally, a maximum pressure of 450 psia (3.1 MPa), 350 psia (2.4 MPa), 250 psia (1.7 MPa), or 150 psia (1.0 MPa). Ranges of pressure which can be utilized to form the metathesis product can range from any minimum pressure to any maximum pressure described herein for metathesis conditions. In some aspects, suitable ranges for the pressure which can be utilized to form the metathesis product (or the liquid metathesis product can include, but are not limited to, from 5 psia (34.5 kPa) to 450 psia (3.10 MPa); alternatively, from 10 psia (68.9 kPa) to 350 psia (2.4 MPa); alternatively, from 14 psia (96.5 kPa) to 250 psi (1.7 MPa); alternatively, from 14 psia (96.5 kPa) to 150 psia (1.0 MPa); alternatively, from 14.7 psia (101.4 kPa) to 150 psia (1.0 MPa); or alternatively, from 20 psia (138.9 kPa) to 150 psia (1.0 MPa). Other pressure ranges which can be utilized to form the metathesis product are readily apparent to those skilled in the art with the aid of this disclosure.

In aspects, the process 100 can utilize any temperature capable of forming a metathesis product in a liquid reaction medium as disclosed herein, where the metathesis product is in liquid phase. In an aspect, the minimum temperature which can be utilized to form the metathesis product can be 30° C., 35° C., 40° C., 45° C., or 50° C.; alternatively or additionally, the maximum temperature which can be utilized to form the metathesis product can be 150° C., 140° C., 130° C., 120° C., 110° C., 90° C., 80° C., 70° C., or 60° C. Ranges for the temperature which can be utilized to form the metathesis product can range from any minimum temperature described herein to any maximum temperature described herein. In some aspects, suitable ranges for the temperature which can be utilized to form the metathesis product can include, but are not limited to, from 30° C. to 150° C.; alternatively, from 35° C. to 100° C.; alternatively, from 40° C. to 90° C.; alternatively, from 45° C. to 80° C.; alternatively, from 50° C. to 70° C.; alternatively, from 50° C. to 65° C.; or alternatively, from 50° C. to 60° C. Other temperature ranges which can be utilized to form the metathesis product (or the liquid metathesis product) are readily apparent to those skilled in the art with the aid of this disclosure.

In aspects, the process 100 can utilize any residence time in the loop reactor 110 (time period or average time period) necessary to form the desired quantity of metathesis product; alternatively, to provide a desired homogeneous metathesis catalyst system productivity; alternatively, to provide a desired conversion (e.g., at least 50 mass %, 60 mass %, 70 mass %, or 80 mass %). In an aspect, the minimum time (or minimum average time) which can be utilized to form the metathesis product can be 1 second, 1 minute, 2 minutes, 4 minutes, 6 minutes, 8 minutes, or 10 minutes; alternatively or additionally, maximum time (or average maximum time) can be 1 hour, 1.5 hours, 2 hours, 4 hours, 6 hours, 8 hours, or 10 hours. Ranges for the time (or average time) which can be utilized to form the metathesis product range from any minimum time to any maximum time described herein for metathesis conditions. In some aspects, suitable ranges for the time (or average time) which can be utilized to form the metathesis product can include, but are not limited to, from 1 second to 10 hours; alternatively, from 1 minute to 8 hours; alternatively, from 2 minutes to 6 hours; alternatively, from 4 minutes to 4 hours; alternatively, from 6 minutes to 2 hours; alternatively, from 8 minutes to 90 minutes; or alternatively, from 10 minutes to 1 hour. Other time (or average time) ranges which can be utilized to form the metathesis product (or the liquid metathesis product) are readily apparent to those skilled in the art with the aid of this disclosure.

In aspects, the process 100 can form metathesis product using any concentration of the homogeneous metathesis catalyst system which can produce the desired quantity of metathesis product, desired metathesis catalyst system productivity, and/or desired conversion a reactant olefin(s) disclosed herein in the desired residence time (or average time). In an aspect, the minimum concentration for the homogeneous metathesis catalyst system can be 100, 200, 300, 400, or 500 ppm by mass; alternatively or additionally, the maximum concentration for the homogeneous metathesis catalyst system can be 1,000, 900, 800, 700, or 600 ppm by mass. Ranges for the concentration of the homogeneous metathesis catalyst system concentration which can be utilized can range from any minimum catalyst system concentration disclosed herein to any maximum catalyst system concentration disclosed herein. In some aspects, suitable ranges for the concentration for the homogeneous metathesis catalyst system which can be utilized to form the metathesis product can include, but are not limited to, 100 to 1,000 ppm, 110 to 900 ppm, 120 to 800 ppm, 130 to 700 ppm, or 130 ppm by mass. Other catalyst system concentration ranges which can be utilized to form the metathesis product are readily apparent to those skilled in the art with the aid of this disclosure. Generally, the ppm basis for the catalyst system concentration can be based upon the mass of the reactant olefin(s).

In aspects, the process 100 can include removing liquid reactor effluent containing metathesis product, unreacted reactant olefin(s), and the homogeneous metathesis catalyst system from the loop reactor 110. The liquid reactor effluent is a portion of the liquid reaction medium circulating in the loop reactor 110. In embodiments, the metathesis product removed in the liquid reactor effluent can contain one product olefin; alternatively, the metathesis product can contain a first product olefin and a second product olefin; alternatively, the metathesis product can contain a first product olefin and a second product olefin, and a third product olefin. In aspects of these embodiments, removal of the liquid reactor effluent from the loop reactor 110 is performed in the process 100 on a continuous basis. In embodiments, the liquid reactor effluent can be removed from the loop reactor 110 via an effluent stream 112.

The reactor effluent stream 112 can be connected to one or more segments 111 of the loop reactor 110, on the discharge side 114b of the circulation pump 114; alternatively, the reactor effluent stream 112 can be connected to the outlet 116 of the circulation pump 114. The reactor effluent stream 112 can include a take-off mechanism to allow or disallow flow of reactor effluent from the loop reactor 110. For example, reactor effluent stream 112 can include one or more continuous take off valves. In some aspects, the reactor effluent stream 112 can be embodied as one or more reactor outlets and associated piping connected to one of segments 111 or to the pump outlet 116, and having one or more continuous take off valve coupled thereto.

The carbon number of the product olefin(s) produced in the loop reactor 110 depends on the reactant olefin(s) that are introduced to the loop reactor 110 and generally include the reaction product of the metathesis reaction that occurs by contact of the reactant olefin(s) in the presence of the homogeneous metathesis catalyst system in the loop reactor 110.

In aspects involving self-metathesis of a single reactant olefin to produce two product olefins, the first product olefin can have a carbon number that is less than a carbon number of the reactant olefin, and the second product olefin can have a carbon number that is greater than the carbon number of the reactant olefin. For example, self-metathesis of 1-butene as the reactant olefin in the presence of the homogeneous metathesis catalyst system can produce ethylene (the first product olefin) and 1-hexene (the second product olefin). In another example, self-metathesis of 1-hexene as the reactant olefin in the presence of the homogeneous metathesis catalyst system can produce ethylene (the first product olefin) and 1-decene (the second product olefin).

Alternatively, in aspects involving cross-metathesis of two reactant olefins to produce a single product olefin, the product olefin can have a carbon number that is less than a carbon number of the first reactant olefin and greater than the carbon number of the second reactant olefin. For example, cross-metathesis of 2-butene (the first reactant olefin) and ethylene (the second reactant olefin) in the presence of the homogeneous metathesis catalyst system can produce propylene (the product olefin).

Alternatively, in aspects involving cross-metathesis of two reactant olefins to produce two product olefins, the first product olefin and the second product olefin can have a carbon number that is greater than a carbon number of the first reactant olefin, and the first product olefin and the second product olefin can have a carbon number that is less than the carbon number of the second reactant olefin. For example, cross-metathesis of ethylene (the first reactant olefin) and diisobutene ($C_8H_{16}$) (the second reactant olefin) in the presence of the homogeneous metathesis catalyst system can produce propylene (the first product olefin) and neohexene ($C_6H_{12}$) (the second product olefin).

Alternatively, in aspects involving cross-metathesis of two reactant olefins to produce two product olefins, the first product olefin can have a carbon number that is less than a carbon number of the first reactant olefin and the second reactant olefin, and the second product olefin can have a carbon number that is greater than the carbon number of the first reactant olefin and less than the carbon number of the second reactant olefin. For example, cross-metathesis of hexene (the first reactant olefin) and octene (the second reactant olefin) in the presence of the homogeneous metathesis catalyst system can produce ethylene (the first product olefin) and heptene (the second product olefin).

Alternatively, in aspects involving cross-metathesis of two reactant olefins to produce three product olefins, the first product olefin can have a carbon number that is less than a carbon number of the first reactant olefin and the second reactant olefin, the second product olefin can have a carbon number that is greater than the carbon number of the first reactant olefin and the second reactant olefin, and the third product olefin can have a carbon number that is greater than the carbon number of the first reactant olefin and the second reactant olefin. For example, cross-metathesis of 1-butene (first reactant olefin) and tetradecene (second reactant olefin) as the reactant olefins in the presence of the homogeneous metathesis catalyst system can produce ethylene (the first product olefin), C16 olefin (the second product olefin), and C26 olefin (the third product olefin).

The process 100 can include introducing the liquid reactor effluent in stream 112 into a first product separation zone 120. The liquid reactor effluent can be continuously or intermittently withdrawn from the loop reactor 110, for example, via a continuous take-off valve or other product takeoff equipment associated with loop reactors. The reactor effluent can flow in reactor effluent stream 112 to the first product separation zone 120.

The process 100 can further include separating, in the first product separation zone 120, the liquid reactor effluent into a first part and a second part. In aspects involving self-metathesis of a reactant olefin to produce two product olefins, the first part can contain the unreacted reactant olefin and the first product olefin, and the second part can contain the unreacted reactant olefin, the second product olefin, and the homogeneous metathesis catalyst system. In aspects involving cross-metathesis of two reactant olefins to produce one product olefin, the first part can contain the first unreacted reactant olefin, the second unreacted reactant olefin, and the first product olefin, and the second part can include the homogeneous metathesis catalyst system. In aspects involving cross-metathesis of two reactant olefins to produce two product olefins, the first part can contain the first unreacted reactant olefin and the first product olefin, and the second part can contain the second unreacted reactant olefin, the second product olefin, and the homogeneous metathesis catalyst system. In aspects involving cross-metathesis of two reactant olefins to produce two product olefins, the first part can contain the first product olefin, and the second part can contain the first unreacted reactant olefin, the second unreacted reactant olefin, the second product olefin, and the homogeneous metathesis catalyst system. In aspects involving cross-metathesis of two reactant olefins to produce three product olefins, the first part can contain the first unreacted reactant olefin and the first product olefin, and the second part can contain the second unreacted reactant olefin, the second product olefin, the third product olefin, and the homogeneous metathesis catalyst system.

The process 100 can further include separating, in the first product separation zone 120, the first part into a first stream 122 and a second stream 126. The first stream 122 can be in liquid phase or in vapor phase. The second stream 126 can be in liquid phase or vapor phase. In aspects involving self-metathesis of a reactant olefin to produce two product olefins, the first stream 122 can contain the first product olefin and the second stream 126 can contain the unreacted reactant olefin. In aspects involving cross-metathesis of two reactant olefins to produce one product olefin, the first stream 122 can contain the first unreacted reactant olefin and the second stream 126 can contain the first product olefin and the second unreacted reactant olefin. In aspects involving cross-metathesis of two reactant olefins to produce two product olefins, the first stream 122 can contain the first product olefin and the second stream 126 can contain the first unreacted reactant olefin. In aspects involving cross-metathesis of two reactant olefins to produce three product olefins, the first stream 122 can contain the first product olefin and the second stream 126 can contain the first unreacted reactant olefin.

In aspects, the process 100 can include recycling the second stream 126 to the loop reactor 110. As described above, the second stream 126 can contain unreacted reactant olefins. The recycled unreacted reactant olefin(s) can be added to the liquid reaction medium circulating in the loop reactor 110 for reaction. Recycling the unreacted reactant olefin(s) to the loop reactor 110 can reduce the amount of fresh reactant olefin needed to achieve a desired production rate of metathesis product.

The process 100 can include introducing the second part in stream 124 into the catalyst separation zone 130, and separating, in the catalyst separation zone, the second part into a third stream 132 and a fourth stream 134 containing the homogeneous metathesis catalyst system. The homogeneous metathesis catalyst system in fourth stream 134 be in the form of spent catalyst or can contain both spent and fresh catalyst.

In aspects involving self-metathesis of a reactant olefin to produce two product olefins, the third stream 132 can contain the unreacted reactant olefin and the second product olefin, and the fourth stream 134 can contain the homogeneous metathesis catalyst system. In aspects involving cross-metathesis of two reactant olefins to produce one product olefin, the second part contains the homogeneous metathesis catalyst system and needs no further separation steps. In aspects involving cross-metathesis of two reactant olefins to produce two product olefins, the third stream 132 can include the second unreacted reactant olefin and the second product olefin, and the fourth stream 134 can contain the homogeneous metathesis catalyst system. In aspects involving cross-metathesis of two reactant olefins to produce three product olefins, the third stream 132 can include the second unreacted reactant olefin, the second product olefin, and the third product olefin, and the fourth stream 134 can contain the homogeneous metathesis catalyst system.

The catalyst separation zone 130 disclosed herein generally includes any equipment configured to separate a mixture containing the product olefin(s) and the homogeneous metathesis catalyst system (e.g., in the form of spent catalyst or containing both spent and fresh catalyst) into a stream containing the homogeneous metathesis catalyst system and a stream containing the product olefin(s). The homogeneous metathesis catalyst system can be separated from the mixture by distillation, membrane separation, conversion of homogeneous catalyst to heterogeneous catalyst, phase separation, or solvent extraction. An example of membrane separation for separating a homogeneous metathesis catalyst from a metathesis reaction mixture is found in U.S. Patent Application Publication No. 2008/0103346.

The process 100 can additionally include introducing the third stream 132 into the second product separation zone 140, and separating, in the second product separation zone 140, the third stream 132 into a fifth stream 144, a sixth stream 142, and optionally a seventh stream 146. The fifth stream 144 can be in liquid phase or in vapor phase. The sixth stream 142 can be in liquid phase or in vapor phase. The seventh stream 146 can be in liquid phase or gas phase, or both liquid and gas phase. In aspects involving self-metathesis of a reactant olefin to produce two product olefins, the fifth stream 144 can contain the unreacted reactant olefin, and the sixth stream 142 can contain the second product olefin. These aspects may not recover components in a seventh stream 146 or may reject (undesired) heavy side product(s) in a seventh stream 146. In aspects involving cross-metathesis of two reactant olefins to produce one product olefin, there may be no separation in a second product separation zone 140. In aspects involving cross-metathesis of two reactant olefins to produce two product olefins, the fifth stream 144 can contain the second unreacted reactant olefin, and the sixth stream 142 can contain the second product olefin. These aspects may not recover components in a seventh stream 146 or may reject (undesired) heavy side product(s) in a seventh stream 146. In aspects involving cross-metathesis of two reactant olefins to produce three product olefins, the fifth stream 144 can contain the second unreacted reactant olefin, the sixth stream 142 can contain the second product olefin, and the seventh stream 146 can contain the third product olefin.

The process 100 can also include recycling the fifth stream 144 to the loop reactor 110. As described above, the fifth stream 144 can contain unreacted reactant olefin. The recycled unreacted reactant olefin can be added to the liquid reaction medium circulating in the loop reactor 110 for reaction. Recycling the unreacted reactant olefin to the loop reactor 110 can reduce the amount of fresh reactant olefin needed to achieve a desired production rate of metathesis product.

FIG. 2 illustrates a schematic diagram of an apparatus 200 for performing the olefin metathesis process 100 of FIG. 1, utilizing a loop reactor 110 for metathesis of one or more reactant olefins to produce one or more product olefins. The apparatus 200 includes the loop reactor 110, the first product separation zone 120, the catalyst separation zone 130, and the second product separation zone 140 of FIG. 1.

In FIG. 2, the first product separation zone 120 includes a first separator 220 and a second separator 225. An inlet to the first separator 220 is connected to the reactor effluent stream 112. A first outlet of the first separator 220 is connected to stream 222, and a second outlet of the first separator 220 is connected to stream 124. An inlet of the second separator 225 is connected to stream 222, a first outlet of the second separator 225 is connected to stream 122, and a second outlet of the second separator 225 is connected to stream 126. Stream 126 is fluidly connected to an inlet of the loop reactor 110, for example, via feed stream 10.

The first separator 220 can be embodied as a vapor liquid separator. Stream 222 can be a top stream of the vapor liquid separator, and stream 124 can be a bottom stream of the vapor liquid separator. In aspects where first separator 220 is a vapor liquid separator, stream 222 can be in vapor phase and stream 124 can be in liquid phase.

In aspects, a temperature and pressure at any point of the first separator 220 are sufficient such that the first product olefin and unreacted reactant olefin are recovered in stream 222 and the second product olefin and the homogeneous metathesis catalyst system is recovered in stream 124. In some aspects, unreacted reactant olefin may also be contained in the stream 124.

The second separator 225 can be embodied as a distillation column or flash tank. In aspects where the second separator 225 is embodied as a distillation column, the distillation column can be embodied as one or more vessels that contain trays, baffles, packing, or other structure configured to distill stream 222 such that the first product olefin flows from the distillation column in vapor phase and the unreacted reactant olefin flows from the distillation column in the liquid phase. In alternative aspects where the second separator 225 is embodied as a distillation column, stream 122 can be in the vapor phase or liquid phase and stream 126 can be in the liquid phase or vapor phase. In aspects where the second separator 225 is embodied as a flash tank, the flash tank can be embodied as one or more vessels such that stream 122 can be in vapor phase and stream 126 can be in liquid phase.

In aspects, a temperature and pressure at any point of the second separator 225 are sufficient such that the first product olefin is recovered in stream 122 and the unreacted reactant olefin is recovered in stream 126.

For the first product separation zone 120 shown in FIG. 2, the process 100 can include receiving, in the first separator 220, the reactor effluent in stream 112 and separating, in the first separator 220, the reactor effluent into a first stream 222 containing the first product olefin and unreacted reactant olefin and a second stream 124 containing the homogeneous metathesis catalyst system, second product olefin, and unreacted reactant olefin. The process 100 can also include receiving, in the second separator 225, stream 222 and separating, in the second separator 225, stream 222 into a third stream 122 containing the first product olefin and a fourth stream 126 containing the unreacted reactant olefin. The process 100 can also include recycling the fourth stream 126 to the loop reactor 110.

The catalyst separation zone 130 can be embodied as any equipment discussed herein and configured to receive stream 124 and to separate stream 124 into stream 134 containing the homogeneous metathesis catalyst system and stream 132 containing unreacted reactant olefin and second product olefin. Stream 132 is connected to the catalyst separation equipment in the catalyst separation zone 130.

In FIG. 2, the second product separation zone 140 includes a separator 240. An inlet of the separator 240 in the second product separation zone 140 is connected to stream 132. A first outlet of the separator 240 is connected to stream 142. A second outlet of the separator 240 is connected to stream 144. A third outlet of the separator 240 is connected to stream 146.

The separator 240 can be embodied as a distillation column, and stream 142 can be a bottoms stream, stream 144 can be a top stream, and stream 146 can be a side draw stream of the distillation column. The distillation column can be embodied as one or more vessels that contain trays, baffles, packing, or other structure(s) configured to distill stream 132 into stream 142, stream 144, and stream 146.

In aspects, a temperature and pressure at any point of the separator 240 are sufficient such that the second product olefin is recovered stream 142 and the unreacted reactant olefin is recovered in stream 144. A mixture of unreacted reactant olefin and the second product olefin can be recovered in stream 146.

For the second product separation zone 140 shown in FIG. 2, the process 100 can include receiving, in the separator 240, stream 132 from the catalyst separation zone 130, and separating, in the separator 240, stream 132 into stream 142 containing the second product olefin, stream 144 containing unreacted reactant olefin, and optionally, stream 146 containing both second product olefin and unreacted reactant olefin.

FIG. 3 illustrates a schematic diagram of an apparatus 300 for performing the olefin metathesis process 100 of FIG. 1, utilizing a loop reactor 110 for metathesis of one or more reactant olefins to produce one or more product olefins. The apparatus 300 includes the loop reactor 110, the first product separation zone 120, the catalyst separation zone 130, and the second product separation zone 140 of FIG. 1.

In FIG. 3, the first product separation zone 120 includes a first separator 220 and a second separator 225. In some aspects, the first product separation zone 120 can include a compressor 221 between the first separator 220 and the second separator 225. An inlet to the first separator 220 is connected to the reactor effluent stream 112. A first outlet of the first separator 220 is connected to stream 222, and a second outlet of the first separator 220 is connected to stream 124. An inlet of the compressor 221 is connected to stream 222, and an outlet of compressor 221 is connected to stream 224. An inlet of the second separator 225 is connected to stream 224, a first outlet of the second separator 225 is connected to stream 122, and a second outlet of the second separator 225 is connected to stream 126. Stream 126 is fluidly connected to an inlet of the loop reactor 110, for example, via feed stream 10.

The first separator 220 can be embodied as a vapor liquid separator. Stream 222 can be a top stream of the vapor liquid separator, and stream 124 can be a bottom stream of the vapor liquid separator. In aspects where first separator 220 is a vapor liquid separator, stream 222 can be in vapor phase and stream 124 can be in liquid phase.

In aspects, a temperature and pressure at any point of the first separator 220 are sufficient such that the first product olefin and first unreacted reactant olefin are recovered in stream 222 and the second product olefin, second unreacted reactant olefin, optional third product olefin, and the homogeneous metathesis catalyst system are recovered in stream 124.

The compressor 221 can be embodied as one or more compressors configured to receive stream 222 and increase a pressure of stream 222 to produce stream 224 having a pressure that is greater than a pressure of stream 222. In aspects, stream 222 is in vapor phase and stream 224 is in liquid phase, vapor phase, or both liquid phase and vapor phase. The compressor 221 is generally configured to increase a pressure of the components in stream 222 from an operating pressure of the first separator 220 to an operating pressure of the second separator 225.

The second separator 225 can be embodied as a distillation column or flash tank. In aspects where the second separator 225 is embodied as a distillation column, the distillation column can be embodied as one or more vessels that contain trays, baffles, packing, or other structure configured to distill stream 224 such that the first product olefin flows from the distillation column in stream 122 in the vapor phase and the first unreacted reactant olefin flows from the distillation column in stream 126 in the liquid phase. In alternative aspects where the second separator 225 is embodied as a distillation column, stream 122 and stream 126 can be in the vapor phase; alternatively, stream 122 and stream 126 can be in the liquid phase. In aspects where the second separator 225 is embodied as a flash tank, the flash tank can be embodied as one or more vessels such that stream 122 can be in vapor phase and stream 126 can be in liquid phase.

In aspects, a temperature and pressure at any point of the second separator 225 are sufficient such that the first product olefin is recovered in stream 122 and the first unreacted reactant olefin is recovered in stream 126.

For the first product separation zone 120 shown in FIG. 3, the process 100 can include receiving, in the first separator 220, the reactor effluent in stream 112 and separating, in the first separator 220, the reactor effluent into a first stream 222 containing the first product olefin and unreacted reactant olefin and a second stream 124 containing the homogeneous metathesis catalyst system, second product olefin, and unreacted reactant olefin. The process 100 can also include receiving, in the compressor 221, stream 222 and compressing, in the compressor 221, stream 222 to form stream 224. The components of stream 222 are the same as components in stream 224. The process 100 can also include receiving, in the second separator 225, stream 224 and separating, in the second separator 225, stream 224 into a third stream 122 containing the first product olefin and a fourth stream 126 containing the unreacted reactant olefin. The process 100 can also include recycling the fourth stream 126 to the loop reactor 110.

The catalyst separation zone 130 can be embodied as any equipment discussed herein and configured to receive stream 124 and to separate stream 124 into stream 134 containing the homogeneous metathesis catalyst system and stream 132 containing unreacted reactant olefin and second product olefin. Stream 132 is connected to the catalyst separation equipment in the catalyst separation zone 130.

In FIG. 3, the second product separation zone 140 includes and a first separator 240 and a second separator 245. An inlet of the separator 240 in the second product separation zone 140 is connected to stream 132. A first outlet of the separator 240 is connected to stream 144. A second outlet of the separator 240 is connected to stream 146a. A third outlet of the separator 240 is connected to stream 242. An inlet of the second separator 245 is connected to stream 242. A first outlet of the second separator 245 is connected to stream 142, a second outlet of the second separator 245 is connected to stream 146b, and a third outlet of the second separator 245 is connected to stream 146c. Stream 146a can contain unreacted reactant olefin (e.g., some of the first unreacted reactant olefin in cross-metathesis). Stream 242 can contain the second product olefin and the third product olefin, as well as some of the second unreacted reactant olefin. Stream 146b can contain unreacted reactant olefin (e.g., some of the second unreacted reactant olefin) and a third product olefin. In these aspects, the first unreacted reactant olefin has smaller carbon number than the carbon number of the second reactant olefin. Stream 146c can contain the third product olefin at a higher concentration than stream 146b.

The first separator 240 can be embodied as a distillation column, and stream 242 can be a bottoms stream, stream 144 can be a side draw stream, and stream 146a can be a top stream of the distillation column. In aspects where the first separator 240 is embodied as a distillation column, the distillation column can be embodied as one or more vessels that contain trays, baffles, packing, or other structure(s) configured to distill stream 132 into stream 242, stream 144, and stream 146a.

In aspects, a temperature and pressure at any point of the first separator 240 are sufficient such that the second unreacted reactant olefin is recovered in stream 144, the first unreacted reactant olefin is recovered stream 146a and the second unreacted reactant olefin, the second product olefin, and optional third product olefin are recovered in stream 242.

The second separator 245 can be embodied as a distillation column, and stream 142 can be a bottoms stream, stream 146b can be a top stream, and stream 146c can be a side draw stream. In aspects where the second separator 245 is embodied as a distillation column, the distillation column can be embodied as one or more vessels that contain trays, baffles, packing, or other structure(s) configured to distill stream 242 into stream 142, stream 146b, and stream 146c.

In aspects, a temperature and pressure at any point of the second separator 245 are sufficient such that the second unreacted reactant olefin and optionally third product olefin are recovered in stream 146b, the third product olefin is recovered in stream 146c, and the second product olefin is recovered in stream 142.

For the second product separation zone 140 shown in FIG. 3, the process 100 can include receiving, in the separator 240, stream 132 from the catalyst separation zone 130, and separating, in the separator 240, stream 132 into i) stream 242 containing the second product olefin, any third product olefin, and any second unreacted reactant olefin, ii) stream 144 containing unreacted reactant olefin (e.g. some of the second unreacted reactant olefin), and stream 146a containing unreacted reactant olefin (e.g., some of the first unreacted reactant olefin). The process 100 can also include recycling stream 144 to the loop reactor 110. The process 100 can also include, receiving, in the second separator 245, stream 242 from the first separator 240, and separating, in the second separator 245, stream 242 into i) stream 142 containing the second product olefin, ii) stream 146b containing unreacted reactant olefin (e.g., some of the second unreacted reactant olefin) and a third product olefin, and stream 146c containing the third product olefin.

EXAMPLES

The following examples are illustrative of a metathesis reaction utilizing a liquid reaction medium with a homogeneous metathesis catalyst system in a loop reactor, and separation of product olefins utilizing a first product separation zone, a catalyst separation zone, and a second product separation zone. Reactant olefin(s) were reacted in liquid phase and in the presence of a homogeneous metathesis catalyst system.

Example 1 is a simulation of self-metathesis of 1-hexene using the apparatus 200 of FIG. 2. 1-hexene was the reactant olefin, ethylene was the first product olefin, decene was the second product olefin, and 1-hexene was the unreacted reactant olefin. The simulation assumed a homogeneous metathesis catalyst system was used.

Stream composition (in wt %), temperature, and flow rate using the stream numbers from apparatus 200 of FIG. 2 are shown in Tables 1A and 1B below:

TABLE 1A

| | Stream | | | | | |
|---|---|---|---|---|---|---|
| | 10 | 112 | 222 | 122 | 124 | 126 |
| T (° C.) | 60 | 60 | 70 | −21.1 | 70 | 60.1 |
| Flow rate (units) | 100 | 1458 | 493 | 17 | 965 | 476 |
| Components (wt %) | | | | | | |
| C2 | — | 1.11 | 3.20 | 90.59 | 0.05 | 0.04 |
| C3 | — | 0.03 | 0.08 | 2.10 | 0.00 | 0.00 |
| C5 | — | 0.04 | 0.07 | 1.32 | 0.03 | 0.03 |
| C6 | 100 | 93.11 | 96.39 | 6.00 | 91.43 | 99.66 |
| C7 | — | 0.05 | 0.03 | 0.00 | 0.06 | 0.03 |
| C9 | — | 0.08 | 0.00 | 0.00 | 0.11 | 0.00 |
| C10 | — | 5.58 | 0.22 | 0.00 | 8.32 | 0.24 |

TABLE 1B

| | Stream | | |
|---|---|---|---|
| | 142 | 144 | 146 |
| T (° C.) | 162.9 | 59.1 | 129 |
| Flow rate (units) | 82 | 882 | 0.5 |
| Components (wt %) | | | |
| C2 | 0.00 | 0.05 | 0.00 |
| C3 | 0.00 | 0.00 | 0.00 |
| C5 | 0.00 | 0.03 | 0.00 |
| C6 | 0.86 | 99.91 | 7.94 |
| C7 | 0.71 | 0.00 | 3.62 |
| C9 | 1.28 | 0.00 | 1.87 |
| C10 | 97.15 | 0.00 | 86.56 |

It should be noted that the reported flow rate of stream 10 above is with regard to the flow of the reactant olefins, and does not include the flow of the homogeneous metathesis catalyst system or the flow of recycled reactant olefins.

In Example 1, the loop reactor 110 operated at 60° C. and 0.3 MPa. The vapor liquid separator 220 was operated at 70° C. and 0.13 MPa. The separator 225 embodied as a distillation column was operated at 0.1 MPa, with 26 stages, a top temperature of −21.1° C., and a bottom temperature of 60.1° C. The separator 240 embodied as a distillation column was operated at 0.1 MPa, with 26 stages, a top temperature of 59.1° C., and a bottom temperature of 162.9° C.

Conversion of 1-hexene was about 7%, and selectivity to ethylene and decene was about 97 wt %.

Example 2 is a simulation of cross-metathesis of 1-butene and 1-tetradecene using the apparatus 300 of FIG. 3. 1-butene was the first reactant olefin, 1-tetradecane was the second reactant olefin, ethylene was the first product olefin, C26 olefin was the second product olefin, C16 was the third product olefin, 1-butene was the first unreacted reactant olefin, and 1-tetradecane was the second unreacted reactant olefin. The simulation assumed a homogeneous metathesis catalyst system was used.

Stream composition (in wt %), temperature, and flow rate using the stream numbers from apparatus 300 of FIG. 3 are shown in Tables 2A and 2B below:

TABLE 2A

| | Stream | | | | | |
|---|---|---|---|---|---|---|
| | 10 | 112 | 224 | 122 | 124 | 126 |
| T (° C.) | 60 | 60 | 186.6 | −17.1 | 70 | 96.2 |
| Flow rate (units) | 100 | 572 | 91 | 11 | 481 | 81 |
| Components (wt %) | | | | | | |
| C2 | — | 2.08 | 12.61 | 94.16 | 0.09 | 1.89 |
| C3 | — | 0.12 | 0.68 | 3.73 | 0.02 | 0.28 |
| C4 | 22.22 | 17.69 | 83.19 | 2.11 | 5.28 | 93.85 |
| C5 | — | 0.10 | 0.31 | 0.00 | 0.06 | 0.35 |
| C6 | — | 1.67 | 3.07 | 0.00 | 1.40 | 3.48 |
| C13 | — | 0.10 | 0.00 | 0.00 | 0.12 | 0.00 |
| C14 | 77.78 | 63.09 | 0.13 | 0.00 | 75.01 | 0.15 |
| C15 | — | 0.35 | 0.00 | 0.00 | 0.41 | 0.00 |
| C16 | — | 8.39 | 0.00 | 0.00 | 9.98 | 0.00 |
| C25 | — | 0.22 | 0.00 | 0.00 | 0.26 | 0.00 |
| C26 | — | 6.19 | 0.00 | 0.00 | 7.36 | 0.00 |

TABLE 2B

| | Stream | | | | | |
|---|---|---|---|---|---|---|
| | 142 | 144 | 146a | 146b | 146c | 242 |
| T (° C.) | 406.2 | 36.5 | 36.5 | 272.2 | 277.3 | 294.2 |
| Flow rate (units) | 36 | 392 | 0.8 | 1.6 | 51 | 89 |
| Components (wt %) | | | | | | |
| C2 | 0.00 | 0.08 | 14.35 | 0.00 | 0.00 | 0.00 |
| C3 | 0.00 | 0.02 | 0.77 | 0.00 | 0.00 | 0.00 |
| C4 | 0.00 | 6.32 | 82.60 | 0.00 | 0.00 | 0.00 |
| C5 | 0.00 | 0.07 | 0.25 | 0.00 | 0.00 | 0.00 |
| C6 | 0.00 | 1.72 | 2.01 | 0.00 | 0.00 | 0.00 |
| C13 | 0.00 | 0.15 | 0.00 | 0.00 | 0.00 | 0.00 |
| C14 | 0.00 | 91.61 | 0.02 | 22.43 | 3.21 | 2.25 |
| C15 | 0.00 | 0.03 | 0.00 | 7.09 | 3.46 | 2.12 |
| C16 | 0.00 | 0.00 | 0.00 | 70.47 | 91.99 | 54.22 |
| C25 | 2.65 | 0.00 | 0.00 | 0.00 | 0.58 | 1.41 |
| C26 | 97.35 | 0.00 | 0.00 | 0.00 | 0.77 | 40.00 |

It should be noted that the reported flow rate of stream 10 above is with regard to the flow of the reactant olefins, and does not include the flow of the homogeneous metathesis catalyst system or the flow of recycled reactant olefins.

In Example 2, the loop reactor 110 operated at 60° C. and 2.0 MPa. The vapor liquid separator 220 was operated at 70° C. and 0.19 MPa. The compressor 221 compressed the vapor in stream 222 from a pressure of 0.19 MPa to a pressure of 2.0 MPa in stream 224. The separator 225 embodied as a distillation column was operated at 2.0 MPa, with 26 stages, a top temperature of −17.1° C., and a bottom temperature of 96.2° C. The separator 240 embodied as a distillation column was operated at 0.1 MPa, with 26 stages, a top temperature of 36.5° C., and a bottom temperature of 294.2° C. The separator 245 embodied as a distillation column was operated at 0.1 MPa, with 16 stages, a top temperature of 272.2° C. and a bottom temperature of 406.2° C.

Conversion of tetradecane was about 19%, and selectivity to ethylene, C16 olefin product, and C26 olefin product was about 94 wt %.

ADDITIONAL DESCRIPTION

Para 1. A process for olefin metathesis in a loop reactor, comprising: circulating, in the loop reactor, a liquid reaction medium comprising a first reactant olefin and a homogeneous metathesis catalyst system; and reacting, in the loop reactor, the first reactant olefin in a presence of the homogeneous metathesis catalyst system to form, in the liquid reaction medium, a metathesis product comprising a first product olefin.

Para 2. The process of Para 1, performed in an apparatus where the loop reactor comprises a plurality of pipe segments and a circulation pump, wherein a flowpath in the loop reactor for the liquid reaction medium is formed by the plurality of pipe segments, wherein an inlet of the circulation pump is fluidly coupled to an outlet of the flowpath, wherein an outlet of the circulation pump is fluidly coupled to an inlet of the flowpath.

Para 3. The process of Para 1 or 2, wherein the loop reactor is liquid full.

Para 4. The process of any of Paras 1 to 3, wherein the homogeneous metathesis catalyst system comprises a metathesis catalyst dissolved in an inert solvent.

Para 5. The process of any of Paras 1 to 4, wherein the homogeneous metathesis catalyst system comprises a metal carbene based metathesis catalyst system.

Para 6. The process of any of Paras 1 to 5, wherein the loop reactor does not include a heterogeneous metathesis catalyst.

Para 7. The process of any of Paras 1 to 6, wherein the metathesis product further comprises a second product olefin.

Para 8. The process of Para 7, further comprising: removing a liquid reactor effluent comprising an unreacted reactant olefin, the first product olefin, the second product olefin, and the homogeneous metathesis catalyst system from the loop reactor; and separating the liquid reactor effluent into i) a first part comprising the unreacted reactant olefin and the first product olefin and ii) a second part comprising the homogeneous metathesis catalyst system, the unreacted reactant olefin, and the second product olefin.

Para 9. The process of Para 8, further comprising: separating the first part into i) a first stream comprising the first product olefin and ii) a second stream comprising the unreacted reactant olefin; and recycling the second stream to the loop reactor.

Para 10. The process of Para 8 or 9, further comprising: separating the second part into i) a third stream comprising the unreacted reactant olefin and the second product olefin and ii) a fourth stream comprising the homogeneous metathesis catalyst system; and separating the third stream into i) a fifth stream comprising the unreacted reactant olefin and ii) a sixth stream comprising the second product olefin.

Para 11. The process of Para 10, further comprising: recycling the fifth stream to the loop reactor.

Para 12. The process of any of Paras 1 to 7, wherein the liquid reaction medium further comprises a second reactant olefin, the process further comprising: reacting, in the loop reactor, the second reactant olefin in the presence of the homogeneous metathesis catalyst system to form the metathesis product; removing a liquid reactor effluent comprising a first unreacted reactant olefin, a second unreacted reactant olefin, the first product olefin, and the homogeneous metathesis catalyst system from the loop reactor; and separating the liquid reactor effluent into i) a first part comprising the first unreacted reactant olefin, the second unreacted reactant olefin, and the first product olefin and ii) a second part comprising the homogeneous metathesis catalyst system.

Para 13. The process of Para 12, further comprising: separating the first part into i) a first stream comprising the first product olefin and ii) a second stream comprising the first unreacted reactant olefin and the second unreacted reactant olefin; and recycling the second stream to the loop reactor.

Para 14. The process of any of Paras 1 to 7, wherein the liquid reaction medium further comprises a second reactant olefin, the process further comprising: reacting, in the loop reactor, the second reactant olefin in the presence of the homogeneous metathesis catalyst system to form the metathesis product, wherein the metathesis product further comprises a second product olefin; removing a liquid reactor effluent comprising a first unreacted reactant olefin, a second unreacted reactant olefin, the first product olefin, the second product olefin, and the homogeneous metathesis catalyst system from the loop reactor; and separating the liquid reactor effluent into i) a first part comprising the first unreacted reactant olefin and the first product olefin and ii) a second part comprising the second unreacted reactant olefin, the second product olefin, and the homogeneous metathesis catalyst system.

Para 15. The process of Para 14, further comprising: separating the first part into i) a first stream comprising the first product olefin and ii) a second stream comprising the first unreacted reactant olefin; and recycling the second stream to the loop reactor.

Para 16. The process of Para 14 or 15, further comprising: separating the second part into i) a third stream comprising the second unreacted reactant olefin and the second product olefin and ii) a fourth stream comprising the homogeneous metathesis catalyst system; and separating the third stream into i) a fifth stream comprising the second unreacted reactant olefin and ii) a sixth stream comprising the second product olefin.

Para 17. The process of Para 16, further comprising: recycling the fifth stream to the loop reactor.

Para 18. The process of any of Paras 1 to 7, wherein the liquid reaction medium further comprises a second reactant olefin, the process further comprising: reacting, in the loop reactor, the second reactant olefin in the presence of the homogeneous metathesis catalyst system to form the metathesis product, wherein the metathesis product further comprises a second product olefin and a third product olefin; removing a liquid reactor effluent comprising a first unreacted reactant olefin, a second unreacted reactant olefin, the first product olefin, the second product olefin, the third product olefin, and the homogeneous metathesis catalyst system from the loop reactor; and separating the liquid reactor effluent into i) a first part comprising the first unreacted reactant olefin and the first product olefin and ii) a second part comprising the second unreacted reactant olefin, the second product olefin, the third product olefin, and the homogeneous metathesis catalyst system.

Para 19. The process of Para 18, further comprising: separating the first part into i) a first stream comprising the first product olefin and ii) a second stream comprising the first unreacted reactant.

Para 20. The process of Para 19, further comprising: recycling the second stream to the loop reactor.

Para 21. The process of Para 19 or 20, further comprising: separating the second part into i) a third stream comprising the second unreacted reactant, the second product olefin, and the third product olefin, and ii) a fourth stream comprising the homogeneous metathesis catalyst system; and separating the third stream into i) a fifth stream comprising the second unreacted reactant, ii) a sixth stream comprising the second product olefin, and iii) a seventh stream comprising the third product olefin.

Para 22. The process of Para 21, further comprising: recycling the fifth stream to the loop reactor.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, processes and steps described in the specification. As one of ordinary skill in the art will readily appreciate from the disclosure, processes, machines, manufacture, compositions of matter, means, processes, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, processes, or steps.

What is claimed is:

1. A process for olefin metathesis in a loop reactor, comprising:
    circulating, in the loop reactor, a liquid reaction medium comprising a first reactant olefin and a homogeneous metathesis catalyst system; and
    reacting, in the loop reactor, the first reactant olefin in a presence of the homogeneous metathesis catalyst system to form, in the liquid reaction medium, a metathesis product comprising a first product olefin.

2. The process of claim 1, wherein the loop reactor comprises a plurality of pipe segments and a circulation pump, wherein a flowpath in the loop reactor for the liquid reaction medium is formed by the plurality of pipe segments, wherein an inlet of the circulation pump is fluidly coupled to an outlet of the flowpath, wherein an outlet of the circulation pump is fluidly coupled to an inlet of the flowpath.

3. The process of claim 1, wherein the loop reactor is liquid full.

4. The process of claim 1, wherein the homogeneous metathesis catalyst system comprises a metathesis catalyst dissolved in an inert solvent.

5. The process of claim 4, wherein the homogeneous metathesis catalyst system comprises a metal carbene based metathesis catalyst system.

6. The process of claim 1, wherein the loop reactor does not include a heterogeneous metathesis catalyst.

7. The process of claim 1, wherein the metathesis product further comprises a second product olefin, the process further comprising:

removing a liquid reactor effluent comprising an unreacted reactant olefin, the first product olefin, the second product olefin, and the homogeneous metathesis catalyst system from the loop reactor; and separating the liquid reactor effluent into i) a first part comprising the unreacted reactant olefin and the first product olefin and ii) a second part comprising the homogeneous metathesis catalyst system, the unreacted reactant olefin, and the second product olefin.

8. The process of claim 7, further comprising:

separating the first part into i) a first stream comprising the first product olefin and ii) a second stream comprising the unreacted reactant olefin; and recycling the second stream to the loop reactor.

9. The process of claim 7, further comprising:

separating the second part into i) a third stream comprising the unreacted reactant olefin and the second product olefin and ii) a fourth stream comprising the homogeneous metathesis catalyst system; and separating the third stream into i) a fifth stream comprising the unreacted reactant olefin and ii) a sixth stream comprising the second product olefin.

10. The process of claim 9, further comprising:

recycling the fifth stream to the loop reactor.

11. The process of claim 1, wherein the liquid reaction medium further comprises a second reactant olefin, the process further comprising:

reacting, in the loop reactor, the second reactant olefin in the presence of the homogeneous metathesis catalyst system to form the metathesis product;

removing a liquid reactor effluent comprising a first unreacted reactant olefin, a second unreacted reactant olefin, the first product olefin, and the homogeneous metathesis catalyst system from the loop reactor; and separating the liquid reactor effluent into i) a first part comprising the first unreacted reactant olefin, the second unreacted reactant olefin, and the first product olefin and ii) a second part comprising the homogeneous metathesis catalyst system.

12. The process of claim 11, further comprising:

separating the first part into i) a first stream comprising the first product olefin and ii) a second stream comprising the first unreacted reactant olefin and the second unreacted reactant olefin; and recycling the second stream to the loop reactor.

13. The process of claim 1, wherein the liquid reaction medium further comprises a second reactant olefin, the process further comprising:

reacting, in the loop reactor, the second reactant olefin in the presence of the homogeneous metathesis catalyst system to form the metathesis product, wherein the metathesis product further comprises a second product olefin;

removing a liquid reactor effluent comprising a first unreacted reactant olefin, a second unreacted reactant olefin, the first product olefin, the second product olefin, and the homogeneous metathesis catalyst system from the loop reactor; and separating the liquid reactor effluent into i) a first part comprising the first unreacted reactant olefin and the first product olefin and ii) a second part comprising the second unreacted reactant olefin, the second product olefin, and the homogeneous metathesis catalyst system.

14. The process of claim 13, further comprising:

separating the first part into i) a first stream comprising the first product olefin and ii) a second stream comprising the first unreacted reactant olefin; and recycling the second stream to the loop reactor.

15. The process of claim 13, further comprising:

separating the second part into i) a third stream comprising the second unreacted reactant olefin and the second product olefin and ii) a fourth stream comprising the homogeneous metathesis catalyst system; and separating the third stream into i) a fifth stream comprising the second unreacted reactant olefin and ii) a sixth stream comprising the second product olefin.

16. The process of claim 15, further comprising:

recycling the fifth stream to the loop reactor.

17. The process of claim 1, wherein the liquid reaction medium further comprises a second reactant olefin, the process further comprising:

reacting, in the loop reactor, the second reactant olefin in the presence of the homogeneous metathesis catalyst system to form the metathesis product, wherein the metathesis product further comprises a second product olefin and a third product olefin;

removing a liquid reactor effluent comprising a first unreacted reactant olefin, a second unreacted reactant olefin, the first product olefin, the second product olefin, the third product olefin, and the homogeneous metathesis catalyst system from the loop reactor; and separating the liquid reactor effluent into i) a first part comprising the first unreacted reactant olefin and the first product olefin and ii) a second part comprising the second unreacted reactant olefin, the second product olefin, the third product olefin, and the homogeneous metathesis catalyst system.

18. The process of claim 17, further comprising:

separating the first part into i) a first stream comprising the first product olefin and ii) a second stream comprising the first unreacted reactant olefin; and recycling the second stream to the loop reactor.

19. The process of claim 17, further comprising:

separating the second part into i) a third stream comprising the second unreacted reactant olefin, the second product olefin, and the third product olefin, and ii) a fourth stream comprising the homogeneous metathesis catalyst system; and separating the third stream into i) a fifth stream comprising the second unreacted reactant olefin, ii) a sixth stream comprising the second product olefin, and iii) a seventh stream comprising the third product olefin.

20. The process of claim 19, further comprising:

recycling the fifth stream to the loop reactor.

* * * * *